US010612050B2

(12) United States Patent
Medoff et al.

(10) Patent No.: US 10,612,050 B2
(45) Date of Patent: *Apr. 7, 2020

(54) PROCESSING BIOMASS

(71) Applicant: XYLECO, INC., Wakefield, MA (US)

(72) Inventors: Marshall Medoff, Wakefield, MA (US); Thomas Craig Masterman, Rockport, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/192,631

(22) Filed: Nov. 15, 2018

(65) Prior Publication Data

US 2019/0085361 A1 Mar. 21, 2019

Related U.S. Application Data

(63) Continuation of application No. 15/884,657, filed on Jan. 31, 2018, now Pat. No. 10,202,621, which is a continuation of application No. 15/387,391, filed on Dec. 21, 2016, now Pat. No. 9,920,335, which is a continuation of application No. 13/177,827, filed on Jul. 7, 2011, now abandoned, which is a continuation of application No. PCT/US2010/020449, filed on Jan. 8, 2010.

(60) Provisional application No. 61/147,377, filed on Jan. 26, 2009.

(51) Int. Cl.
| | | |
|---|---|---|
| *C12P 7/40* | (2006.01) | |
| *C12P 7/62* | (2006.01) | |
| *C12P 7/06* | (2006.01) | |
| *C12P 7/10* | (2006.01) | |
| *C12P 7/04* | (2006.01) | |
| *C12P 7/54* | (2006.01) | |
| *C12P 7/56* | (2006.01) | |
| *C13K 1/02* | (2006.01) | |
| *C13K 1/06* | (2006.01) | |
| *C12P 7/14* | (2006.01) | |
| *C12P 7/46* | (2006.01) | |

(52) U.S. Cl.
CPC ............... *C12P 7/10* (2013.01); *C12P 7/04* (2013.01); *C12P 7/065* (2013.01); *C12P 7/14* (2013.01); *C12P 7/40* (2013.01); *C12P 7/46* (2013.01); *C12P 7/54* (2013.01); *C12P 7/56* (2013.01); *C12P 7/62* (2013.01); *C13K 1/02* (2013.01); *C13K 1/06* (2013.01); *C10J 2300/1612* (2013.01); *C10J 2300/1665* (2013.01); *C10J 2300/1681* (2013.01); *Y02E 50/16* (2013.01); *Y02E 50/17* (2013.01); *Y02T 50/678* (2013.01)

(58) Field of Classification Search
CPC ......... C12P 7/10; C12P 2203/00; C12P 19/14; C12P 19/02; C12P 7/04; C12P 7/62; C12P 5/02; C12P 5/023; C12N 9/16; C12N 1/20
USPC .............. 435/135, 41, 132, 160, 162, 252.2, 435/254.11
See application file for complete search history.

(56) References Cited

U.S. PATENT DOCUMENTS

| | | |
|---|---|---|
| 3,801,432 A | 4/1974 | Free |
| 6,140,545 A | 10/2000 | Merger et al. |
| 7,109,005 B2 | 9/2006 | Eroma et al. |
| 7,504,245 B2 | 3/2009 | Kinley et al. |
| 7,781,191 B2 | 8/2010 | Dunson, Jr. et al. |
| 7,932,065 B2 | 4/2011 | Medoff |
| 8,329,436 B2 | 12/2012 | Verser et al. |
| 2005/0136520 A1 | 6/2005 | Kinley et al. |
| 2007/0014895 A1 | 1/2007 | Holtzapple et al. |
| 2007/0275447 A1 | 11/2007 | Lewis et al. |
| 2010/0248318 A1 | 9/2010 | Granda et al. |
| 2010/0279361 A1 | 11/2010 | South et al. |

FOREIGN PATENT DOCUMENTS

| | | |
|---|---|---|
| CA | 2859623 | 6/2008 |
| EP | 0645456 | 3/1995 |
| EP | 1130085 | 9/2001 |
| JP | 60-251897 | 12/1985 |
| JP | 63-167795 | 7/1988 |
| JP | 2002-003386 A | 1/2002 |

(Continued)

OTHER PUBLICATIONS

Khan, A.W. et al., "Effect of Electron-Beam Irradiation Pretreatment on the Enzymatic Hydrolysis of Softwood", Biotechnology and Bioengineering, Wiley & Sons, Hoboken, NJ, US, vol. 28, No. 9, Jan. 1, 1986, pp. 1449-1453.

(Continued)

*Primary Examiner* — Robert B Mondesi
*Assistant Examiner* — Mohammad Y Meah
(74) *Attorney, Agent, or Firm* — Leber IP Law; Carol A. Egner

(57) ABSTRACT

Carbon-containing materials, such as biomass (e.g., plant biomass, animal biomass, and municipal waste biomass) or coal are processed to produce useful products, such as fuels, carboxylic acids and equivalents thereof (e.g., esters and salts). For example, systems are described that can use feedstock materials, such as cellulosic and/or lignocellulosic materials and/or starchy materials, to produce ethanol, butanol or organic acids (e.g., acetic or lactic acid), salts of organic acids or mixtures thereof. If desired, organic acids can be converted into alcohols, such as by first converting the acid, salt or mixtures of the acid and its salt to an ester, and then hydrogenating the formed ester. Acetogens or homoacetogens which are capable of utilizing a syngas from a thermochemical conversion of coal or biomass can be utilized to produce the desired product.

13 Claims, 10 Drawing Sheets

(56) References Cited

FOREIGN PATENT DOCUMENTS

| JP | 2006045366 | 2/2006 |
|---|---|---|
| JP | 2007112669 | 5/2007 |
| JP | 2007298290 | 11/2007 |
| WO | 2000053791 | 9/2000 |
| WO | 2005040392 | 5/2005 |
| WO | 2005118826 | 12/2005 |
| WO | 2007112090 | 10/2007 |
| WO | 2008098254 | 8/2008 |
| WO | 2008137639 | 11/2008 |
| WO | 2009/102609 A1 | 8/2009 |

OTHER PUBLICATIONS

Khan, A.W. et al., "Electron Beam Irradiation Pretreatment and Enzymatic Saccharification of Used Newsprint and Paper Mill Wastes", International Journal of Radiation Applications and Instrumentation, Part C, Radiation Physics and Chemistry, Pergamon, vol. 29, No. 2, Jan. 1, 1987, pp. 117-120.
Search Report—Corresponding European Application No. 10733750, dated Mar. 17, 2016, 13 pages.
Smith, G.S. et al., Irradiation Enhancement of Biomass Conversion:, Radial. Phys. Chem., vol. 25, Nos. 1-3, pp. 27-33, 1985.
Search Report—Corresponding European Application No. 10733750, dated Aug. 24, 2016, 28 pages.
Bentivenga et al., Biomass and Bioenergy 2003, 24, pp. 233-238.
Dyk et al., Intl. J. Coal Tech. 2006, 65, pp. 243-253.
Search Report—Corresponding PCT Application No. PCT/US10/020449, dated Aug. 30, 2010, 5 pages.
Written Opinion—Corresponding PCT Application No. PCT/US10/020449, dated Aug. 30, 2010, 5 pages.
Bak et al., Bioresource Technology, 2009, 11 pp. 1285-1290, available online on Oct. 17, 2008.
Indian Patent Application No. 201818015145 Examination Report dated Oct. 15, 2019 with English translation, 6 pages.
English Translation of Japanese Patent Application No. JP-2017-079394 Notice of Reasons for Rejection dated Jun. 24, 2019, 3 pages.

PROCESSING BIOMASS

RELATED APPLICATIONS

This application is a continuation of U.S. application Ser. No. 15/884,657, filed Jan. 31, 2018, U.S. Pat. No. 10,202,621, which is a continuation of U.S. application Ser. No. 15/387,391, filed Dec. 21, 2016, U.S. Pat. No. 9,920,335, which is a continuation of U.S. application Ser. No. 13/177,827, filed Jul. 7, 2011, abandoned, which is a continuation of PCT/US2010/020449, filed Jan. 8, 2010, which claims the benefit of U.S. Provisional Application No. 61/147,377, filed on Jan. 26, 2009. The entirety of each of these applications is incorporated herein by reference.

TECHNICAL FIELD

This invention relates to processing biomass and products made therefrom.

BACKGROUND

Various carbohydrates, such as cellulosic and lignocellulosic materials, e.g., in fibrous form, are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,307,108, 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, AND "FIBROUS MATERIALS AND COMPOSITES," U.S. Patent Application Publication No. 2007/0045456.

SUMMARY

Generally, this invention relates to carbon-containing materials, such as carbohydrate-containing materials (e.g., starchy materials and/or cellulosic or lignocellulosic materials), methods of making and processing such materials to change their structure and/or their recalcitrance level, and products made from the changed materials. For example, many of the methods described herein can provide cellulosic and/or lignocellulosic materials that have a lower recalcitrance level, a lower molecular weight, a different level of functionalization and/or crystallinity relative to a native material. Many of the methods provide materials that can be more readily utilized by a variety of microorganisms, such as one or more homoacetogens or heteroacetogens (with or without enzymatic hydrolysis assistance) to produce useful products, such as hydrogen, alcohols (e.g., ethanol or butanol), organic acids (e.g., acetic acid and/or lactic acid), hydrocarbons, co-products (e.g., proteins, such as single cell proteins) or mixtures of any of these.

Many of the products obtained, such as ethanol or n-butanol, can be utilized directly as a fuel or as a blend with other components, such as gasoline, for powering cars, trucks, tractors, ships or trains, e.g., as an internal combustion fuel or as a fuel cell feedstock. Other products described herein (e.g., organic acids, such as acetic acid and/or lactic acid) can be converted to other moieties (e.g., esters or anhydrides) that can be converted and utilized as a fuel. Many of the products obtained can also be utilized to power aircraft, such as planes, e.g., having jet engines, or helicopters. In addition, the products described herein can be utilized for electrical power generation, e.g., in a conventional steam generating plant or in a fuel cell plant.

Exemplary products that can be produced by employing the methods described herein include hydrocarbons, proteins, alcohols (e.g., a monohydric alcohols or a dihydric alcohols), such as ethanol, n-propanol or n-butanol, carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid and olefins, such as ethylene. Specific examples include ethanol, propanol, propylene glycol, butanol, 1,4-butanediol, 1,3-propanediol, methyl or ethyl esters of any of these alcohols, methyl acrylate, methylmethacrylate, lactic acid, propionic acid, butyric acid, succinic acid, 3-hydroxypropionic acid, a salt of any of the acids and a mixture of any of the acids and respective salts.

In one aspect, the invention features methods of making an alcohol, a carboxylic acid, a salt of a carboxylic acid, an ester of a carboxylic acid, or a mixture of any of these. The methods include treating a carbon-containing material, such a biomass material or coal, with any treatment method described herein, such as with one or more of radiation, sonication, pyrolysis, oxidation and steam explosion; and converting at least a portion of the treated carbon-containing material utilizing a microorganism to produce a product that includes one or more of an alcohol, a carboxylic acid, a salt of a carboxylic acid, a carboxylic acid ester or a mixture of any of these. The methods can further include acidifying, esterifying and/or hydrogenating the product. For example, acetogens or homoacetogens, which are capable of utilizing a syngas from a thermochemical conversion process, can be utilized to enhance the efficiency of the conversion.

In another aspect, the invention features methods of making one or more alcohols that include treating a carbon-containing material, such as a biomass material and/or coal, with one or more of radiation, sonication, pyrolysis, oxidation and steam explosion; converting at least a portion of the treated carbon-containing material utilizing a microorganism, such as one or more acetogens or homoacetogens which are capable of utilizing a syngas from the thermochemical conversion of coal or biomass, to a product that includes a carboxylic acid, a salt of a carboxylic acid, a carboxylic acid ester or a mixture of any of these; and hydrogenating the product to produce alcohol.

Carbon dioxide generated and/or lignin liberated in any process described herein can be captured. Any captured carbon dioxide can be sequestered, e.g., by injecting the captured carbon dioxide into a geological formation capable of maintaining the carbon dioxide, e.g., for a period of time greater than 100 years, e.g., greater than 250 years, 500 years, 1,000 years or greater than 10,000 years. For example, any carbon dioxide produced in any process described herein can be sequestered, e.g., by fixing carbon dioxide utilizing any microorganism described herein. For example, the microorganism can include algae and the carbon dioxide can be sequestered in the form of a carbohydrate and/or lipid. If desired, e.g., to produce a bio-diesel, the lipid can be converted into an ester, e.g., a methyl, ethyl or propyl ester.

Changing a molecular structure of a material, as used herein, means to change the chemical bonding arrangement or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or changing an overall domain size.

All publications, patent applications, patents, and other references mentioned herein or attached hereto are incorporated by reference in their entirety for all that they contain.

DESCRIPTION OF THE DRAWINGS

FIG. 12 is a schematic drawing a fuel production process utilizing algae, while

DETAILED DESCRIPTION

Figure 1:
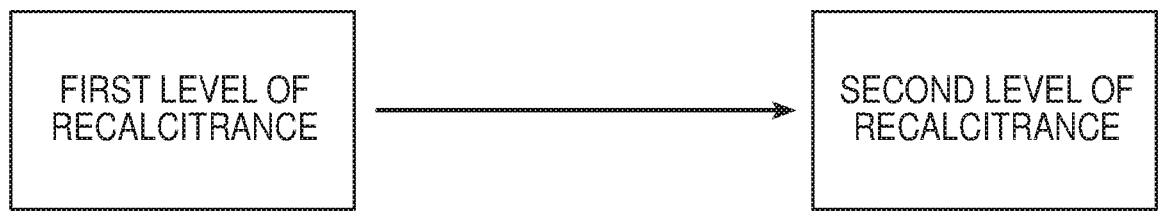
FIG. 1 is a schematic diagram illustrating a process for reducing recalcitrance of a recalcitrant material.

Carbon-containing materials, such as biomass (e.g., coal, plant biomass, animal biomass, and municipal waste biomass) can be processed to a lower level of recalcitrance (if necessary) and converted into useful products such as organic acids, salts of organic acids, anhydrides, esters of organic acids and fuels, e.g., fuels for internal combustion engines or feedstocks for fuel cells. Systems and processes are described herein that use readily abundant, but often difficult to process, materials, such as pre-coal or coal, e.g., peat, lignite, sub-bituminous, bituminous and anthracite, oil sand, oil shale or cellulosic or lignocellulosic materials. Many of the processes described herein can effectively lower the recalcitrance level of any carbon-containing material, such as any carbon-containing material described herein, making it easier to process, such as by bioprocessing (e.g., with any microorganism described herein, such as a homoacetogen or a heteroacetogen, and/or any enzyme described herein), thermal processing (e.g., gasification, cracking or pyrolysis) or chemical methods (e.g., acid hydrolysis or oxidation). Generally, if required, materials can be physically treated for processing and/or after processing, often by size reduction. Physically processed feedstock can be treated or processed using one or more of any of the methods described herein, such as radiation, sonication, oxidation, pyrolysis or steam explosion. The various treatment systems and methods can be used in combinations of two, three, or even four of these technologies or others described herein and elsewhere.

In some cases, to provide materials that include a carbohydrate, such as cellulose or hemicellulose, that can be converted by a microorganism to a number of desirable products, such as combustible fuels (e.g., ethanol, butanol or hydrogen), organic acids or anhydrides, feedstocks that include one or more saccharide units can be treated by any one or more of the processes described herein. Other products and co-products that can be produced include, e.g., human food, animal feed, pharmaceuticals, and nutriceuticals. When organic acids are prepared first, such acids can be converted to other intermediates (e.g., esters and anhydrides), and then converted to alcohols by hydrogenation, e.g., high-pressure hydrogenation, such as at a pressure of between about 25 bar and 700 bar, e.g., 50 to 500 bar, or 100 to 400 bar, in the presence of a catalyst, such as copper chromite catalyst, cobalt catalysts, zinc catalysts or palladium catalysts. Hydrogenation of esters is discussed in Wall, R. G., U.S. Pat. No. 4,113,662. Preparing organic acids can have benefits relative to making alcohols directly in some instances (e.g., in terms of carbon utilization efficiency), as will be described further herein. In some embodiments, acetogens or homoacetogens, which are capable of utilizing a syngas from a thermochemical conversion process, can be utilized to enhance the efficiency of the conversion.

Figure 1A:
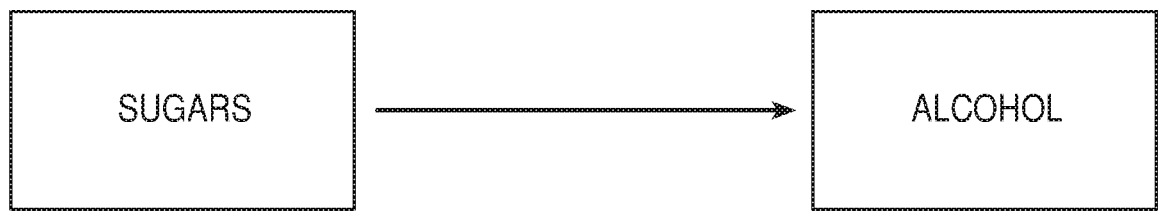
FIG. 1A is a schematic diagram illustrating conversion of sugars derived from biomass into ethanol.
Figure 1B:
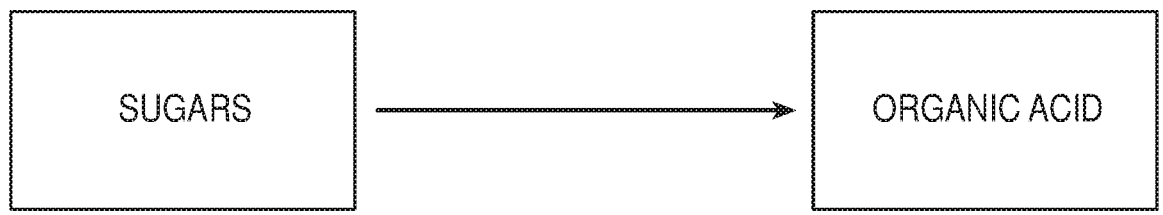
FIG. 1B is a schematic diagram illustrating conversion of sugars derived from biomass into an organic acid.

Referring to FIG. 1, in some instances and when necessary, a first material, such as a lignocellulosic material, having a first level of recalcitrance is processed, such as by treating with a beam of particles, such as electrons, to produce a second material having a second level of recalcitrance lower than the first level of recalcitrance. At this point and if necessary, the second material can be hydrolyzed, e.g., using enzymes, to its constituent sugars, such as glucose, xylose and arabinose. Referring now to FIGS. 1A and 1B collectively, the sugars can be converted directly into an alcohol by a microorganism, such as a one or more bacteria or yeasts, such as *Saccharomyces cerevisiae* and/or *Pichia stipitis*, or the sugars can be converted to an organic acid, such as acetic acid and/or lactic acid. If desired, the organic acid can be converted to an ester, and then the ester hydrogenated under a high pressure of hydrogen and in the presence of a catalyst to liberate alcohol.

Examples of Biomass

Generally, any biomass material that is or includes carbohydrates composed entirely of one or more saccharide units or that includes one or more saccharide units can be processed by any of the methods described herein, such as being processed to reduce its level of recalcitrance. For example, the biomass material can include one or more cellulosic or lignocellulosic materials, or starchy materials, such as kernels of corn, grains of rice or other foods.

For example, such materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these.

For example, the biomass can be fibrous in nature. Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton. Fiber sources can be obtained from virgin scrap textile materials, e.g., remnants, post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105.

In some embodiments, the carbohydrate is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

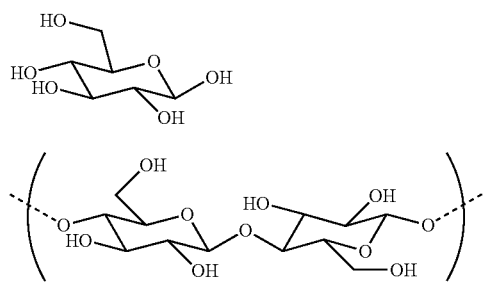

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. In particular embodiments, the starchy material is derived from corn. Various corn starches and derivatives are described in "Corn Starch," Corn Refiners Association (11$^{th}$ Edition, 2006).

Examples of Other Carbon-Containing Materials and Blends

Pre-coal or coal, e.g., peat, lignite, sub-bituminous, bituminous and anthracite, oil sand, oil shale can also be utilized as carbon sources. In addition, blends of any biomass materials described herein and any other carbon-containing material described herein can be utilized for making any of the products described herein, such as ethanol, acetic acid or ethyl acetate.

Physical Preparation

In some cases, methods can include a physical preparation, e.g., size reduction of materials, such as by cutting, grinding, shearing, pulverizing or chopping. For example, in some cases, loose feedstock (e.g., recycled paper, starchy materials, coal or switchgrass) is prepared by shearing or shredding. For example, in other cases, material is first pretreated or processed using one or more any of the methods described herein, such as radiation, sonication, oxidation, pyrolysis or steam explosion, and then size reduced or further size reduced. Treating first and then size reducing can be advantageous since treated materials tend to be more brittle and, therefore, easier to size reduce. Screens and/or magnets can be used to remove oversized or undesirable objects such as, for example, rocks or nails from the feed stream.

Feed preparation systems can be configured to produce streams with specific characteristics such as, for example, specific maximum sizes, specific length-to-width, or specific surface areas ratios. Physical preparation can increase the rate of reactions or reduce the processing time required by opening up the materials and making them more accessible to processes and/or reagents, such as reagents in a solution. The bulk density of feedstocks can be controlled (e.g., increased). In some situations, it can be desirable to prepare a low bulk density material, densify the material (e.g., to make it easier and less costly to transport to another site), and then revert the material to a lower bulk density state.

Size Reduction

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (¹⁄₁₆ inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source. The shredded fiber source is sheared between stationary blades and rotating blades to provide a first fibrous material. The first fibrous material passes through a screen, and the resulting second fibrous material is captured in a bin. To aid in the collection of the second fibrous material, the bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source is utilized to maintain the bin below nominal atmospheric pressure.

Shearing can be advantageous for "opening up" and "stressing" the fibrous materials, making the cellulose of the materials more susceptible to chain scission and/or reduction of crystallinity. The open materials can also be more susceptible to oxidation when irradiated.

The fiber source can be sheared in a dry state (e.g., having little or no free water on its surface), a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol or isopropanol.

The fiber source can also be sheared under a gas (such as a stream or atmosphere of gas other than air), e.g., oxygen or nitrogen, or steam.

Other methods of making the fibrous materials include, e.g., stone grinding, mechanical ripping or tearing, pin grinding or air attrition milling.

If desired, the fibrous materials can be separated, e.g., continuously or in batches, into fractions according to their length, width, density, material type, or some combination of these attributes. For example, for forming composites, it is often desirable to have a relatively narrow distribution of fiber lengths.

The fibrous materials can also be separated, e.g., by using a high velocity gas, e.g., air. In such an approach, the fibrous materials are separated by drawing off different fractions, which can be characterized photonically, if desired. Such a separation apparatus is discussed in Lindsey et al, U.S. Pat. No. 6,883,667.

Ferrous materials can be separated from any of the fibrous materials by passing a fibrous material that includes a ferrous material past a magnet, e.g., an electromagnet, and then passing the resulting fibrous material through a series of screens, each screen having different sized apertures.

The fibrous materials can be irradiated immediately following their preparation, or they can may be dried, e.g., at approximately 105° C. for 4-18 hours, so that the moisture content is, e.g., less than about 0.5% before use.

If desired, lignin can be removed from any of the fibrous materials that include lignin. Also, to aid in the breakdown of the materials that include cellulose, the material can be treated prior to irradiation with heat, a chemical (e.g., mineral acid, base or a strong oxidizer such as sodium hypochlorite) and/or an enzyme.

In some embodiments, the average opening size of the first screen is less than 0.79 mm ($\frac{1}{32}$ inch, 0.03125 inch), e.g., less than 0.51 mm ($\frac{1}{50}$ inch, 0.02000 inch), less than 0.40 mm ($\frac{1}{64}$ inch, 0.015625 inch), less than 0.23 mm (0.009 inch), less than 0.20 mm ($\frac{1}{128}$ inch, 0.0078125 inch), less than 0.18 mm (0.007 inch), less than 0.13 mm (0.005 inch), or even less than less than 0.10 mm ($\frac{1}{256}$ inch, 0.00390625 inch). The screen can be prepared, e.g., by interweaving monofilaments having an appropriate diameter to give the desired opening size. For example, the monofilaments can be made of a metal, e.g., stainless steel. As the opening sizes get smaller, structural demands on the monofilaments may become greater. For example, for opening sizes less than 0.40 mm, it can be advantageous to make the screens from monofilaments made from a material other than stainless steel, e.g., titanium, titanium alloys, amorphous metals, nickel, tungsten, rhodium, rhenium, ceramics, or glass. In some embodiments, the screen is made from a plate, e.g. a metal plate, having apertures, e.g., cut into the plate using a laser. In some embodiments, the open area of the mesh is less than 52%, e.g., less than 41%, less than 36%, less than 31% or less than 30%.

A third fibrous material can be prepared from the second fibrous material by shearing the second fibrous material and passing the resulting material through a second screen having an average opening size less than the first screen.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g. greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (e.g., diameter) of the second fibrous material 14 can be, e.g., between about 5 μm and 50 rpm, e.g., between about 10 μm and 30 μm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$.

A porosity of the second fibrous material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material to the average length-to-diameter ratio of the second fibrous material is, e.g., less than 1.5, less than 1.4, less than 1.25, less than 1.1, less than 1.075, less than 1.05, less than 1.025, or even substantially equal to 1.

In particular embodiments, the second fibrous material is sheared again and the resulting fibrous material passed through a second screen having an average opening size less than that of the first screen to provide a third fibrous material. In such instances, a ratio of the average length-to-diameter ratio of the second fibrous material to the average length-to-diameter ratio of the third fibrous material can be, e.g., less than 1.5, e.g., less than 1.4, less than 1.25, or even less than 1.1.

In some embodiments, the third fibrous material is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

Densification

Densified materials can be processed by any of the methods described herein, or any material processed by any of the methods described herein can be subsequently densified.

A material, e.g., a processed or unprocessed fibrous material, having a low bulk density can be densified to a product having a higher bulk density. For example, a material composition having a bulk density of 0.05 g/cm$^3$ can be densified by sealing the fibrous material in a relatively gas impermeable structure, e.g., a bag made of polyethylene, a bag made of alternating layers of polyethylene and a nylon, or a bag made of a dissolvable material such as a starch-based film, and then evacuating the entrapped gas, e.g., air, from the structure. After evacuation of the air from the structure, the fibrous material can have a bulk density of, e.g., greater than 0.3 g/cm$^3$, 0.5 g/cm$^3$, 0.6 g/cm$^3$, 0.7 g/cm$^3$ or more, e.g., 0.85 g/cm$^3$. Prior to and/or after densification, the product can be processed by any of the methods described herein, such as irradiated, e.g., with gamma radiation. This can be advantageous when it is desirable to transport the material to another location, e.g., a remote manufacturing plant, where the fibrous material composition can be added to a solution, e.g., to produce ethanol. After cutting or piercing the substantially gas impermeable structure, the densified fibrous material can revert to nearly its initial bulk density, e.g., greater than 60 percent of its initial bulk density, e.g., 70 percent, 80 percent, 85 percent or more, e.g., 95 percent of its initial bulk density. To reduce static electricity in the fibrous material, an anti-static agent can be added to the material.

In some embodiments, the structure, e.g., bag, is formed of a material that dissolves in a liquid, such as water. For example, the structure can be formed from a polyvinyl alcohol so that it dissolves when in contact with a water-based system. Such embodiments allow densified structures to be added directly to solutions that include a microorganism, without first releasing the contents of the structure, e.g., by cutting or piercing.

Any material, e.g., biomass material, can be combined with any desired additives and a binder, and subsequently densified by application of pressure, e.g., by passing the material through a nip defined between counter-rotating pressure rolls or by passing the material through a pellet mill. During the application of pressure, heat can optionally be applied to aid in the densification of the fibrous material. The densified material can then be irradiated.

In some embodiments, the material prior to densification has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

The preferred binders include binders that are soluble in water, swollen by water, or that have a glass transition temperature of less than 25° C., as determined by differential scanning calorimetry. By water-soluble binders, we mean binders having a solubility of at least about 0.05 weight percent in water. By water swellable binders, we mean binders that increase in volume by more than 0.5 percent upon exposure to water.

In some embodiments, the binders that are soluble or swollen by water include a functional group that is capable of forming a bond, e.g., a hydrogen bond, with the fibers of the fibrous material, e.g., cellulosic fibrous material. For example, the functional group can be a carboxylic acid group, a carboxylate group, a carbonyl group, e.g., of an aldehyde or a ketone, a sulfonic acid group, a sulfonate group, a phosphoric acid group, a phosphate group, an amide group, an amine group, a hydroxyl group, e.g., of an alcohol, and combinations of these groups, e.g., a carboxylic acid group and a hydroxyl group. Specific monomeric examples include glycerin, glyoxal, ascorbic acid, urea, glycine, pentaerythritol, a monosaccharide or a disaccharide, citric acid, and tartaric acid. Suitable saccharides include glucose, sucrose, lactose, ribose, fructose, mannose, arabinose and erythrose. Polymeric examples include polyglycols, polyethylene oxide, polycarboxylic acids, polyamides, polyamines and polysulfonic acids and polysulfonates. Specific polymeric examples include polypropylene glycol (PPG), polyethylene glycol (PEG), polyethylene oxide, e.g., POLYOX®, copolymers of ethylene oxide and propylene oxide, polyacrylic acid (PAA), polyacrylamide, polypeptides, polyethylenimine, polyvinylpyridine, poly(sodium-4-styrenesulfonate) and poly(2-acrylamido-methyl-1-propanesulfonic acid).

In some embodiments, the binder includes a polymer that has a glass transition temperature of less 25° C. Examples of such polymers include thermoplastic elastomers (TPEs). Examples of TPEs include polyether block amides, such as those available under the tradename PEBAX®, polyester elastomers, such as those available under the tradename HYTREL®, and styrenic block copolymers, such as those available under the tradename KRATON®. Other suitable polymers having a glass transition temperature less 25° C. include ethylene vinyl acetate copolymer (EVA), polyolefins, e.g., polyethylene, polypropylene, ethylene-propylene copolymers, and copolymers of ethylene and alpha olefins, e.g., 1-octene, such as those available under the tradename ENGAGE®.

In a particular embodiment, the binder is a lignin, e.g., a natural or synthetically modified lignin.

A suitable amount of binder added to the material, calculated on a dry weight basis, is, e.g., from about 0.01 percent to about 50 percent, e.g., 0.03 percent, 0.05 percent, 0.1 percent, 0.25 percent, 0.5 percent, 1.0 percent, 5 percent, 10 percent or more, e.g., 25 percent, based on a total weight of the densified material. The binder can be added to the material as a neat, pure liquid, as a liquid having the binder dissolved therein, as a dry powder of the binder, or as pellets of the binder.

The densified fibrous material can be made in a pellet mill. The material, after densification, can be conveniently in the form of pellets or chips having a variety of shapes. The pellets can then be irradiated or otherwise treated by any method described herein. In some embodiments, the pellets or chips are cylindrical in shape, e.g., having a maximum transverse dimension of, e.g., 1 mm or more, e.g., 2 mm, 3 mm, 5 mm, 8 mm, 10 mm, 15 mm or more, e.g., 25 mm. Pellets can be made so that they have a hollow inside. The hollow can be generally in-line with the center of the pellet, or out of line with the center of the pellet. Making the pellet hollow inside can increase the rate of dissolution in a liquid.

The pellet can have, e.g., a transverse shape that is multi-lobal, e.g., tri-lobal as shown, or tetra-lobal, penta-lobal, hexa-lobal or deca-lobal. Making the pellets in such transverse shapes can also increase the rate of dissolution in a solution.

Treatment to Solubilize, Reduce Recalcitrance or to Functionalize

Materials that have or have not been physically prepared can be treated for use in any production process described herein. Treatment processes can include one or more of any of those described herein, such as irradiation, sonication, oxidation, pyrolysis or steam explosion. Treatment methods can be used in combinations of two, three, four, or even all of these technologies (in any order).

Radiation Treatment

One or more radiation processing sequences can be used to process materials from a wide variety of different sources to extract useful substances from the feedstock, and to provide partially degraded organic material, which functions as input to further processing steps and/or sequences. Irradiation can reduce the molecular weight and/or crystallinity and/or recalcitrance of a feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock.

The doses applied depend on the desired effect and the particular feedstock. For example, high doses of radiation can break chemical bonds within feedstock components. In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce a fuel or other useful product that is or includes hydrogen, an alcohol (e.g., ethanol or butanol, such as n-, sec- or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing a microorganism and/or an enzyme. These properties make the second material more susceptible to chemical, enzymatic and/or biological attack relative to the first material, which can greatly improve the production rate and/or production level of a desired product, e.g., ethanol. Radiation can also sterilize the materials or any media needed to bioprocess the material.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodatron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria. Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate materials, such as carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Doses

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

SONICATION

One or more sonication processing sequences can be used to process materials from a wide variety of different sources to extract useful substances from the materials, and to provide partially degraded organic material (when organic materials are employed) which functions as input to further processing steps and/or sequences. Sonication can reduce the molecular weight and/or crystallinity of the materials, such as one or more of any of the materials described herein, e.g., one or more carbohydrate sources, such as cellulosic or lignocellulosic materials, or starchy materials.

In one method, a first material that includes cellulose having a first number average molecular weight ($M_{N1}$) is dispersed in a medium, such as water, and sonicated and/or otherwise cavitated, to provide a second material that includes cellulose having a second number average molecular weight ($M_{N2}$) lower than the first number average molecular weight. The second material (or the first and second material in certain embodiments) can be combined with a microorganism (with or without enzyme treatment) that can utilize the second and/or first material to produce a fuel that is or includes hydrogen, an alcohol, an organic acid, a hydrocarbon or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material more susceptible to chemical, enzymatic, and/or microbial attack relative to the first material, which can greatly improve the production rate and/or production level of a desired product, e.g., ethanol. Sonication can also sterilize the materials, but should not be used while the microorganisms are supposed to be alive.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Without wishing to be bound by any particular theory, it is believed that sonication breaks bonds in the carbon-containing material by creating bubbles in the medium containing the cellulose, which grow and then violently collapse. During the collapse of the bubble, which can take place in less than a nanosecond, the implosive force raises the local temperature within the bubble to about 5100 K (even higher in some instances; see, e.g., Suslick et al., Nature 434, 52-55) and generates pressures of from a few hundred atmospheres to over 1000 atmospheres or more. It is believed that these high temperatures and pressures that break the bonds.

In addition, without wishing to be bound by any particular theory, it is believed that reduced crystallinity arises, at least in part, from the extremely high cooling rates during collapse of the bubbles, which can be greater than about $10^{11}$ K/second. The high cooling rates generally do not allow the cellulose to organize and crystallize, resulting in materials that have reduced crystallinity. Ultrasonic systems and sonochemistry are discussed in, e.g., Olli et al., U.S. Pat. No. 5,766,764; Roberts, U.S. Pat. No. 5,828,156; Mason, Chemistry with Ultrasound, Elsevier, Oxford, (1990); Suslick (editor), Ultrasound: its Chemical, Physical and Biological Effects, VCH, Weinheim, (1988); Price, "Current Trends in Sonochemistry" Royal Society of Chemistry, Cambridge, (1992); Suslick et al., Ann. Rev. Mater. Sci. 29, 295, (1999); Suslick et al., Nature 353, 414 (1991); Hiller et al., Phys. Rev. Lett. 69, 1182 (1992); Barber et al., Nature, 352, 414 (1991); Suslick et al., J. Am. Chem. Soc., 108, 5641 (1986); Tang et al., Chem. Comm., 2119 (2000); Wang et al., Advanced Mater., 12, 1137 (2000); Landau et al., J. of Catalysis, 201, 22 (2001); Perkas et al., Chem. Comm., 988 (2001); Nikitenko et al., Angew. Chem. Inter. Ed. (December 2001); Shafi et al., J. Phys. Chem B 103, 3358 (1999); Avivi et al., J. Amer. Chem. Soc. 121, 4196 (1999); and Avivi et al., J. Amer. Chem. Soc. 122, 4331 (2000).

Pyrolysis

One or more pyrolysis processing sequences can be used to process carbon-containing materials from a wide variety of different sources to extract useful substances from the materials, and to provide partially degraded materials which function as input to further processing steps and/or sequences.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight. The second material (or the first and second material in certain embodiments) is/are combined with a microorganism (with or without acid or enzymatic hydrolysis) that can utilize the second and/or first material to produce a fuel that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material more susceptible to chemical, enzymatic and/or microbial attack relative to the first material, which can greatly improve the production rate and/or production level of a desired product, e.g., ethanol. Pyrolysis can also sterilize the first and second materials.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material has cellulose that has as crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process carbon-containing materials from a wide variety of different sources to extract useful substances from the materials, and to provide partially degraded and/or altered material which functions as input to further processing steps and/or sequences.

In one method, a first material that includes cellulose having a first number average molecular weight ($M_{N1}$) and having a first oxygen content ($O_1$) is oxidized, e.g., by heating the first material in a stream of air or oxygen-enriched air, to provide a second material that includes cellulose having a second number average molecular weight ($M_{N2}$) and having a second oxygen content ($O_2$) higher than the first oxygen content ($O_1$).

Such materials can also be combined with a solid and/or a liquid. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Fuels and coproducts are described in FIBROUS MATERIALS AND COMPOSITES," U.S. Ser. No. 11/453,951, filed Jun. 15, 2006. The entire contents of each of the foregoing applications are incorporated herein by reference.

In some embodiments, the second number average molecular weight is not more 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight.

The amount of reduction of molecular weight will depend upon the application. For example, in some preferred embodiments that provide composites, the second number average molecular weight is substantially the same as the first number average molecular weight. In other applications, such as making ethanol or another fuel or coproduct, a higher amount of molecular weight reduction is generally preferred.

In some embodiments in which the materials are used to make a fuel or a coproduct, the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace.

Without wishing to be bound by any particular theory, it is believed that oxidation increases the number of hydrogen-bonding groups on the material, e.g., a lignocellulosic or cellulosic material. Examples of such hydrogen-bonding groups include hydroxyl groups, aldehyde groups, ketone group, carboxylic acid groups or anhydride groups Such groups can increase the material's dispersability and/or its solubility (e.g., in a liquid).

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance in a carbon-containing material, such as coal or cellulosic or lignocellulosic materials, employ Fenton or Fenten-type chemistry. Fenten-type chemistry is discussed in Pestovsky et al., Angew. Chem., Int. Ed. 2005, 44, 6871-6874, the entire disclosure of which is hereby incorporated by reference herein. Generally, to utilize such methods, a first material, such as a cellulosic or lignocellulosic material, having a first level of recalcitrance is provided and combined with one or more compounds that include one or more naturally-occurring, non-radioactive group 5, 6, 7, 8, 9, 10 or 11 elements to provide a mixture. Optionally, one or more oxidants capable of increasing an oxidation state of at least some of the elements are also combined with the mixture. The mixture is permitted to contact the material and such contact is maintained for a period of time and under conditions sufficient to produce a second material, such as a cellulosic or lignocellulosic material, having a second level of recalcitrance lower than the first level of recalcitrance.

In some embodiments, the one or more elements are in a 1+, 2+, 3+, 4+ or 5+ oxidation state. In particular instances, the one or more elements include Mn, Fe, Co, Ni, Cu or Zn, preferably Fe or Co. For example, the Fe or Co can be in the form of a sulfate, e.g., iron(II) or iron(III) sulfate. In particular instances, the one or more elements are in a 2+, 3+ or 4+ oxidation state. For example, iron can be in the form of iron(II), iron(III) or iron(IV).

Exemplary iron (II) compounds include ferrous sulfate heptahydrate, iron(II) acetylacetonate, (+)-iron(II) L-ascorbate, iron(II) bromide, iron(II) chloride, iron(II) chloride hydrate, iron(II) chloride tetrahydrate, iron(II) ethylenediammonium sulfate tetrahydrate, iron(II) fluoride, iron(II) gluconate hydrate, iron(II) D-gluconate dehydrate, iron(II) iodide, iron(II) lactate hydrate, iron(II) molybdate, iron(II) oxalate dehydrate, iron(II) oxide, iron(II,III) oxide, iron(II) perchlorate hydrate, iron(II) phthalocyanine, iron(II) phthalocyanine bis(pyridine) complex, iron(II) sulfate heptahydrate, iron(II) sulfate hydrate, iron(II) sulfide, iron(II) tetrafluoroborate hexahydrate, iron(II) titanate, ammonium iron(II) sulfate hexahydrate, ammonium iron(II) sulfate, cyclopentadienyl iron(II) dicarbonyl dimmer, ethylenediaminetetraacetic acid hydrate iron(III) sodium salt and ferric citrate.

Exemplary iron (III) compounds include iron(III) acetylacetonate, iron(III) bromide, iron(III) chloride, iron(III) chloride hexahydrate, iron(III) chloride solution, iron(III)

chloride on silica gel, iron(III) citrate, tribasic monohydrate, iron(III) ferrocyanide, iron(III) fluoride, iron(III) fluoride trihydrate, iron(III) nitrate nonahydrate, iron(III) nitrate on silica gel, iron(III) oxalate hexahydrate, iron(III) oxide, iron(III) perchlorate hydrate, iron(III) phosphate, iron(III) phosphate dehydrate, iron(III) phosphate hydrate, iron(III) phosphate tetrahydrate, iron(III) phthalocyanine chloride, iron(III) phthalocyanine-4,4',4'',4'''-tetrasulfonic acid, compound with oxygen hydrate monosodium salt, iron(III) pyrophosphate, iron(III) sulfate hydrate, iron(III) p-toluenesulfonate hexahydrate, iron(III) tris(2,2,6,6-tetramethyl-3,5-heptanedionate) and ammonium iron(III) citrate.

Exemplary cobalt (II) compounds include cobalt(II) acetate, cobalt(II) acetate tetrahydrate, cobalt(II) acetylacetonate hydrate, cobalt(II) benzoylacetonate, cobalt(II) bromide, cobalt(II) bromide hydrate and cobalt(II) carbonate hydrate.

Exemplary cobalt (III) compounds include cobalt(III) acetylacetonate, cobalt(III) fluoride, cobalt(III) oxide, cobalt (III) sepulchrate trichloride, hexammine cobalt(III) chloride, bis(cyclopentadienyl)cobalt(III) hexafluorophosphate and bis(ethylcyclopentadienyl)cobalt(III) hexafluorophosphate.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Conditions can also include a contact period of between 2 and 12 hours, e.g., between 4 and 10 hours or between 5 and 8 hours. In some instances, conditions include not exceeding 300° C., e.g., not exceeding 250, 200, 150, 100 or 50° C. In special desirable instances, the temperature remains substantially ambient, e.g., at or about 20-25° C.

In some desirable embodiments, the one or more oxidants are applied to a first cellulosic or lignocellulosic material and the one or more compounds as a gas, such as by generating ozone in-situ by irradiating the first cellulosic or lignocellulosic material and the one or more compounds through air with a beam of particles, such as electrons.

In particular desirable embodiments, a first cellulosic or lignocellulosic material is firstly dispersed in water or an aqueous medium that includes the one or more compounds dispersed and/or dissolved therein, water is removed after a soak time (e.g., loose and free water is removed by filtration), and then the one or more oxidants are applied to the combination as a gas, such as by generating ozone in-situ by irradiating the first cellulosic or lignocellulosic and the one or more compounds through air with a beam of particles, such as electrons (e.g., each being accelerated by a potential difference of between 3 MeV and 10 MeV). Soaking can open up interior portions to oxidation.

In some embodiments, the mixture includes one or more compounds and one or more oxidants, and a mole ratio of the one or more compounds to the one or more oxidants is from about 1:1000 to about 1:25, such as from about 1:500 to about 1:25 or from about 1:100 to about 1:25.

In some desirable embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some desirable embodiments, the one or more oxidants are electrochemically-generated in-situ. For example, hydrogen peroxide and/or ozone can be electrochemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, acid treatment (including concentrated and dilute acid treatment with mineral acids, such as sulfuric acid, hydrochloric acid and organic acids, such as trifluoroacetic acid), base treatment (e.g., treatment with lime or sodium hydroxide), UV treatment, screw extrusion treatment (see, e.g., U.S. Patent Application Ser. No. 61/073, 530, filed Nov. 18, 2008, solvent treatment (e.g., treatment with ionic liquids) and freeze milling (see, e.g., U.S. Patent Application Ser. No. 61/081,709).

Thermochemical Conversion

A thermochemical conversion process includes changing molecular structures of carbon-containing material at elevated temperatures. Specific examples include gasification, pyrolysis, reformation, partial oxidation and mixtures of these (in any order).

Gasification converts carbon-containing materials into a synthesis gas (syngas), which can include methanol, carbon monoxide, carbon dioxide and hydrogen. Many microorganisms, such as acetogens or homoacetogens are capable of utilizing a syngas from the thermochemical conversion of coal or biomass, to produce a product that includes an alcohol, a carboxylic acid, a salt of a carboxylic acid, a carboxylic acid ester or a mixture of any of these. Gasification of carbonaceous materials, such as coal and biomass (e.g., cellulosic or lignocellulosic materials), can be accomplished by a variety of techniques. For example, gasification can be accomplished utilizing staged steam reformation with a fluidized-bed reactor in which the carbonaceous material is first pyrolyzed in the absence of oxygen and then the pyrolysis vapors are reformed to synthesis gas with steam providing added hydrogen and oxygen. In such a technique, process heat comes from burning char. Another technique utilizes a screw auger reactor in which moisture (and oxygen) are introduced at the pyrolysis stage and the process heat is generated from burning some of the gas produced in the latter stage. Another technique utilizes entrained flow reformation in which both external steam and air are introduced in a single-stage gasification reactor. In partial oxidation gasification, pure oxygen is utilized with no steam.

Production of Fuels Acids, Esters and/or Other Products

A typical biomass resource contains cellulose, hemicellulose, and lignin plus lesser amounts of proteins, extractables and minerals. As described herein, the complex carbohydrates contained in the cellulose and hemicellulose fractions can be processed into fermentable sugars using the treatment processes described herein, optionally, along with acid or enzymatic hydrolysis. Also as discussed herein, the sugars liberated can be converted into a variety of products, such as alcohols or organic acids. The product obtained depends upon the microorganism utilized and the conditions under which the bioprocessing occurs.

$$C_6H_{12}O_6 \rightarrow 3CH_3COOH$$

For example, when a homoacetogen is used to convert glucose into acetate, acetic acid or mixtures thereof (represented by the equation directly below), the reaction has nearly a 100% carbon yield and the resulting acetate contains about 94% of the chemical energy of the initial glucose (ignoring cell mass production). Chemical energy efficiency is defined as the ratio of the heat of combustion of the products divided by the heat of combustion of the feeds, times 100 to convert into a percentage. For example, taking values from Table 3.7 of Roels, J. A., Energetics and Kinetics in Biotechnology, Elsevier Biomedical, 1983, the heat of combustion (HHV basis) of glucose and acetic acid are 2807 KJ/mol and 876 kJ/mol, respectively, so the chemical energy efficiency for this reaction is $(3 \times 876/2807) \times 100 = 93.4\%$.

Many bacteria, such as anaerobic bacteria, are capable of fermenting syngas components (CO, $H_2$, $CO_2$) into useful products. Table 1 shows that many homoacetogens will produce acetate from syngas mixtures at about 77% chemical efficiency. Another class of bacteria, known as heteroacetogens, can produce ethanol directly from syngas mixtures at chemical energy efficiencies of about 80%. The literature has many more examples of bacteria, such as anaerobic bacteria, capable of metabolizing both sugar and syngas feedstocks. For example, the Acetonema and Eubacterium (Butyribacterium) can produce mixtures of acetate and butyric acids from many of the materials described herein.

TABLE 1

Examples of chemical energy efficiencies of homoacetogens and heteroacetogens

| | Chemical Energy Efficiency, % |
|---|---|
| Homoacetogens | |
| $4CO + 2H_2O \rightarrow CH_3COOH + 2CO_2$ | 77.4 |
| $2CO + 2H_2 \rightarrow CH_3COOH$ | 77.0 |
| $2CO_2 + 4H_2 \rightarrow CH_3COOH + 2H_2O$ | 76.6 |
| Heteroacetogens - Ethanol as Major Product | |
| $6CO + 3H_2O \rightarrow CH_3CH_2OH + 4CO_2$ | 80.6 |
| $2CO + 4H_2 \rightarrow CH_3CH_2OH + H_2O$ | 80.1 |
| $2CO_2 + 6H_2 \rightarrow CH_3CH_2OH + 3H_2O$ | 79.8 |

(computations based on values in Roels, J.A., Energetics and Kinetics in Biotechnology, Elsevier Biomedical, 1983)

Typical exemplary products from such homoacetogen or heteroacetogen conversion (e.g., fermentation) include acetate, propionate, butyrate, hydrogen, carbon dioxide, and methane. A pure culture of one or more homoacetogens can be used to drive most of the products to acetate. This acetate can then be recovered as an organic salt or organic acid, or further transformed into an aldehyde, ester, alcohol or alkene. The resulting organic acid mixture can be recovered and/or transformed into organic acid salts, acids, aldehydes, esters, alcohols, alkenes. If desired, the mixtures can be separated into relatively pure fractions.

Both sugar and syngas pathways in acetogens and other bacteria can be utilized to drive the carbon and chemical energy of any feedstock material described herein into acetate or any other product or coproduct described herein (actual products and coproducts depending upon microorganism and conditions utilized). One advantage of utilizing both sugars and syngas for conversion is that this removes any restrictions on the maximum obtainable energy efficiency caused by limitations in the amount of carbon present in the feedstock material in the form of fermentable and/or complex carbohydrates. This is especially useful for biomass feedstock materials with relatively low levels of energy in the form of carbohydrates, such as high lignin lignocellulosic material.

Generally, various microorganisms can produce a number of useful products, such as a fuel, by operating on, e.g., fermenting the treated carbon-containing materials.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized. The microorganism can be an aerobe or an anaerobe. The microorganism can be a homofermentative microorganism (produces a single or a substantially single end product). The microorganism can be a homoacetogenic microorganism, a homolactic microorganism, a propionic acid bacterium, a butyric acid bacterium, a succinic acid bacterium or a 3-hydroxypropionic acid bacterium. The microorganism can be of a genus selected from the group *Clostridium, Lactobacillus, Moorella, Thermoanaerobacter, Proprionibacterium, Propionispera, Anaerobiospirillum*, and *Bacteroides*. In specific instances, the microorganism can be *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteroides amylophilus* or *Bacteroides ruminicola*. For example, the microorganism can be a recombinant microorganism engineered to produce a desired product, such as a recombinant *Escherichia coli* transformed with one or more genes capable of encoding proteins that direct the production of the desired product is used (see, e.g., U.S. Pat. No. 6,852,517, issued Feb. 8, 2005).

Other microorganisms include strains of the genus *Saccharomyces* spp. e.g., *Saccharomyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech), GERT STRAND® (available from Gert Strand AB, Sweden) and FERMOL® (available from DSM Specialties).

Bacteria that can ferment biomass to ethanol and other products include, e.g., *Zymomonas mobilis* and *Clostridium thermocellum* (Philippidis, 1996, supra). Leschine et al. (*International Journal of Systematic and Evolutionary Microbiology* 2002, 52, 1155-1160) isolated an anaerobic, mesophilic, cellulolytic bacterium from forest soil, *Clostridium phytofermentans* sp. nov., which converts cellulose to ethanol.

Fermentation of biomass to ethanol and other products may be carried out using certain types of thermophilic or genetically engineered microorganisms, such *Thermoanaerobacter* species, including *T. mathranii*, and yeast species such as *Pichia* species. An example of a strain of *T. mathranii* is A3M4 described in Sonne-Hansen et al. (*Applied Microbiology and Biotechnology* 1993, 38, 537-541) or Ahring et al. (*Arch. Microbiol.* 1997, 168, 114-119).

To aid in the breakdown of the materials that include the cellulose (treated by any method described herein or even untreated), one or more enzymes, e.g., a cellulolytic enzyme can be utilized. In some embodiments, the materials that include the cellulose are first treated with the enzyme, e.g., by combining the material and the enzyme in an aqueous solution. This material can then be combined with any microorganism described herein. In other embodiments, the materials that include the cellulose, the one or more enzymes and the microorganism are combined concurrently, e.g., by combining in an aqueous solution.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

A cellulase is capable of degrading biomass and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Other methods utilize one or more ligninases and/or biomass-destroying enzymes to reduce recalcitrance in cellulosic or lignocellulosic materials. In such methods, a first cellulosic or lignocellulosic material having a first level of recalcitrance is provided and combined with one or more ligninases and/or one or more biomass-destroying, e.g., lignin-destroying organisms, so as to contact the first cellulosic or lignocellulosic material. The contact is maintained for a period of time, such as between 2 and 24 hours, e.g., between 6 and 12 hours, and under conditions sufficient, e.g., below a pH of about 6, such as between pH 3 and 5.5, to produce a second lignocellulosic material having a second level of recalcitrance lower than the first level of recalcitrance. After reduction of the recalcitrance, the second cellulosic or lignocellulosic material can be contacted with one or more enzymes and/or microorganisms, e.g., to make any product described herein, e.g., food or fuel, e.g., ethanol or butanol (e.g., n-butanol) or any product described in any application incorporated by reference herein.

The ligninase can be, e.g., one or more of manganese peroxidase, lignin peroxidase or laccases.

In particular implementations, the biomass-destroying organism can be, e.g., one or more of white rot, brown rot or soft rot. For example, the biomass-destroying organism can be a Basidiomycetes fungus. In particular embodiments, the biomass-destroying organism is *Phanerochaete chrysoporium* or *Gleophyllum trabeum*.

Ligninases, biomass-destroying organisms and small molecule metabolites are described in Kirk et al., Enzyme Microb. Technol. 1986, vol. 8, 27-32, Kirk et al., Enzymes for Pulp and Paper Processing, Chapter 1 (Roles for Microbial Enzymes in Pulp and Paper Processing and Kirk et al., The Chemistry of Solid Wood, Chapter 12 (Biological Decomposition of Solid Wood (pp. 455-487).

Figure 2:
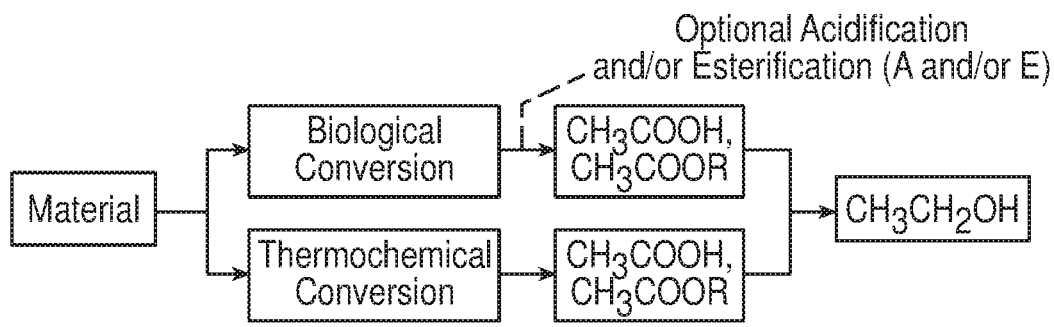
FIG. 2 is a schematic diagram illustrating a process for making ethanol.

Referring now to FIG. 2, one method of producing ethanol from a material that includes carbon-containing compounds, such as a lignocellulosic material treated with accelerated electrons in which less than about 75% by weight of the carbon-containing compounds are in the form of carbohydrates, includes biologically converting (with or without enzymatic assistance) a portion of the material into acetic acid, an acetate ester (e.g., a methyl or ethyl ester), an acetate salt, or a mixture of acetic acid, acetate ester and acetate salt (shown as simply $CH_3COOH$ and $CH_3COOR$ in the figure) and converting another portion of the material using a thermochemical process (gasification) to produce a syngas (a mixture of hydrogen, carbon monoxide, and in some instances, carbon dioxide or a component thereof (often referred to as a reducing gas)—shown in the figure as $H_2$). The syngas or a component thereof is then reacted with the acetic acid, acetate ester, acetate salt, or a mixture of acetic acid, acetate ester and acetate salt, e.g., in the presence of a catalyst and under a high pressure of hydrogen (e.g., 50 bar to 700 bar) to produce ethanol. The chemical energy efficiency of this method to produce ethanol can be greater than the chemical energy efficiency of either a solely biological conversion process or a conversion process in which all of the material is initially subjected to a thermochemical conversion step as part of the process to produce ethanol.

In some instances, acid and/or acid salt is (are) the product(s) produced by the biological process. In such instances, the acid and/or acid salt can be treated by acidification and/or esterification prior to the step of reacting with a thermochemical process-produced intermediate. For example, an intermediate produced by the biological process can include a salt of a carboxylic acid, which can be acidified to the carboxylic acid. For example, the biological process-produced intermediate can include a carboxylic acid that can be esterified, with methanol or ethanol to form the corresponding carboxylic acid esters. Acidification and esterification can be accomplished by biological or chemical means. For example, in one embodiment, acidifying can include introducing carbon dioxide or an acid with a lower pKa than the carboxylic acid being acidified to a solution that includes the salt of the carboxylic acid. In another embodiment, acidifying can include introducing a tertiary amine with carbon dioxide to form an acid/amine complex. This process can further include contacting the acid/amine complex with a water immiscible solvent to form an ester of the water immiscible solvent and the carboxylic acid. Methods of acidification and esterification are described in more detail in WO 2005/073161 published on Aug. 11, 2005 and in WO 00/53791 published on Sep. 14, 2000.

Figure 3:
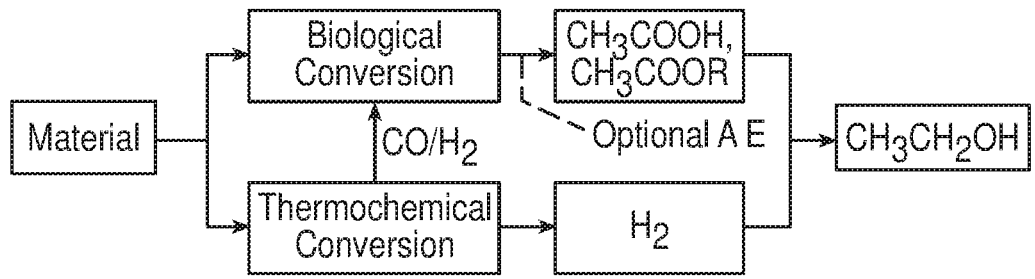
FIG. 3 is a schematic diagram illustrating another process for making ethanol.

Referring to FIG. 3, another method of producing ethanol from a material that includes carbon-containing compounds, such as a lignocellulosic material treated with ozone or Fenton's solution, includes biologically converting (without or without enzymatic assistance) a portion of the material into acetic acid, an acetate ester, an acetate salt, or a mixture of acetic acid, acetate ester and acetate salt (shown as simply $CH_3COOH$ and $CH_3COOR$ in the figure) and converting another portion of the material using a thermochemical process (gasification) to produce a syngas. A portion of the syngas in the form of carbon monoxide and hydrogen is fed into the biological process during conversion. Another portion of the syngas (hydrogen) is utilized to react with the acetic acid, acetate ester, acetate salt, or a mixture of acetic acid, acetate ester and acetate salt, e.g., in the presence of a catalyst and under a high pressure of hydrogen (e.g., 25 or 50 bar to 700 bar) to produce ethanol.

Figure 4:
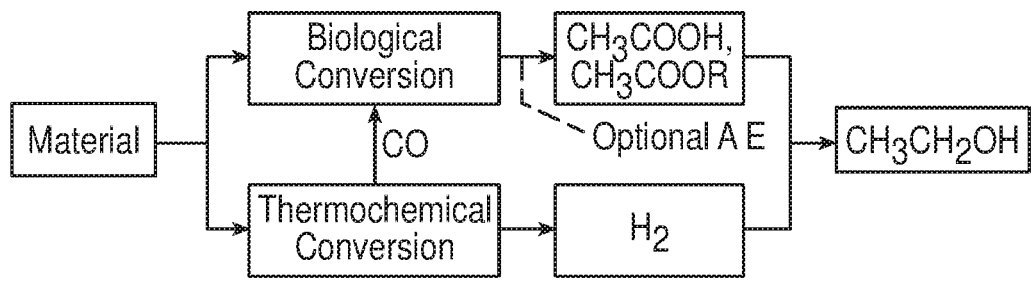
FIG. 4 is a schematic diagram illustrating another process for making ethanol.

Referring to FIG. 4, another method of producing ethanol from a material that includes carbon-containing compounds, such as a lignocellulosic material sonicated to reduce its recalcitrance, includes biologically converting (without or without enzymes being present) a portion of the material into acetic acid, an acetate ester, an acetate salt, or a mixture of acetic acid, acetate ester and acetate salt (shown as simply $CH_3COOH$ and $CH_3COOR$ in the figure) and converting another portion of the material using a thermochemical process (gasification) to produce a syngas. A portion of the syngas in the form of carbon monoxide is fed into the biological conversion process. Another portion of the syngas in the form of hydrogen is utilized to react with the acetic acid, acetate ester, acetate salt, or a mixture of acetic acid, acetate ester and acetate salt to produce ethanol.

Figure 5:
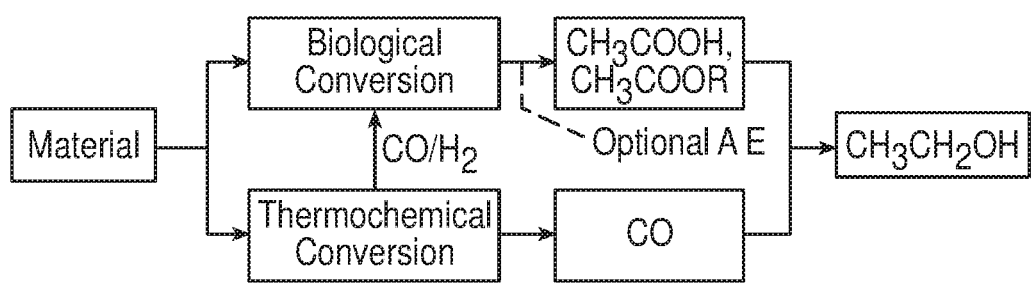
FIG. 5 is a schematic diagram illustrating another process for making ethanol.

Referring to FIG. 5, another method of producing ethanol from a material that includes carbon-containing compounds, such as a lignocellulosic material pyrolyzed to reduce its recalcitrance, includes biologically converting (without or without enzymes being present) a portion of the material into acetic acid, an acetate ester, an acetate salt, or a mixture of acetic acid, acetate ester and acetate salt (shown as simply $CH_3COOH$ and $CH_3COOR$ in the figure) and converting another portion of the material using a thermochemical process (gasification) to produce a syngas. A portion of the syngas in the form of carbon monoxide and hydrogen is fed into the biological conversion process. Another portion of the syngas in the form of carbon monoxide is utilized to react with the acetic acid, acetate ester, acetate salt, or a mixture of acetic acid, acetate ester and acetate salt to produce ethanol.

Figure 6:
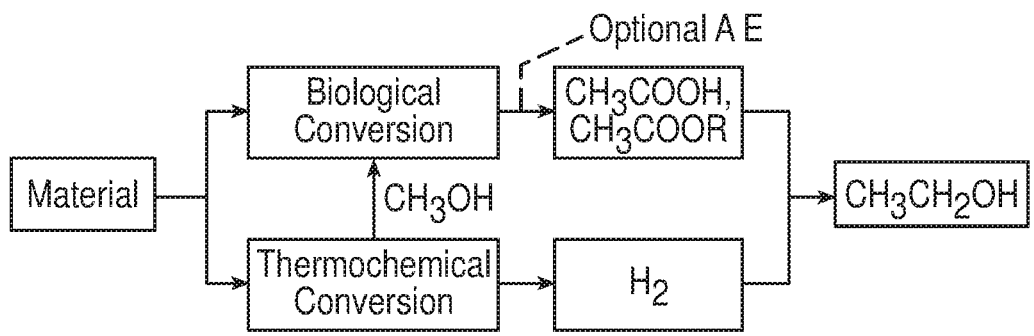
FIG. 6 is a schematic diagram illustrating another process for making ethanol.

Referring to FIG. 6, another method of producing ethanol from a material that includes carbon-containing compounds, such as coal pyrolyzed to reduce its recalcitrance, includes biologically converting (without or without enzymes being present) a portion of the material into acetic acid, an acetate ester, an acetate salt, or a mixture of acetic acid, acetate ester and acetate salt (shown as simply $CH_3COOH$ and $CH_3COOR$ in the figure) and converting another portion of the material using a thermochemical process (gasification) to produce a syngas that includes hydrogen and methanol. A portion of the syngas in the form of methanol ($CH_3OH$) is fed into the biological conversion process. Another portion of the syngas in the form of hydrogen is utilized to react with the acetic acid, acetate ester, acetate salt, or a mixture of acetic acid, acetate ester and acetate salt to produce ethanol.

Figure 7:
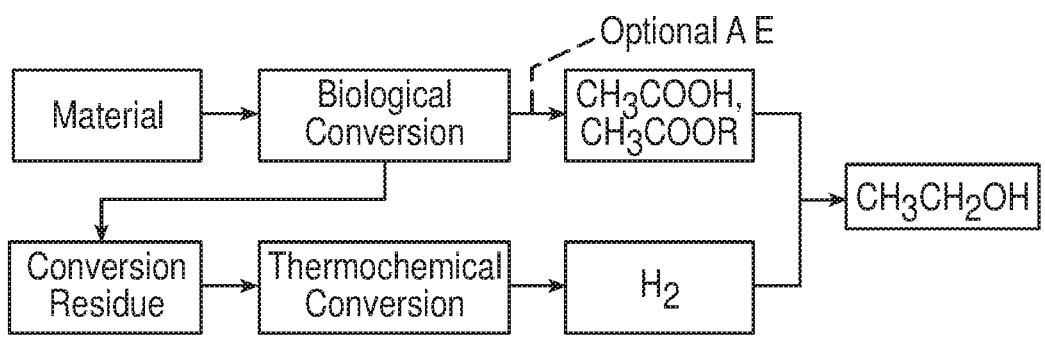
FIG. 7 is a schematic diagram illustrating utilizing biological conversion residue in a process for making ethanol.

Referring to FIG. 7, another method of producing ethanol from a material that includes carbon-containing compounds, such as a lignocellulosic material treated with ozone or Fenton's solution and/or irradiated with electrons, includes biologically converting (without or without enzymes being present) the entire portion of the material that is biologically convertible into acetic acid, an acetate ester, an acetate salt, or a mixture of acetic acid, acetate ester and acetate salt (shown as simply $CH_3COOH$ and $CH_3COOR$ in the figure). The conversion residue, e.g., the lignin portion of the lignocellulosic material, is then converted using a thermochemical process (e.g., gasification) to produce a syngas. A portion of the syngas in the form of hydrogen is utilized to react with the acetic acid, acetate ester, acetate salt, or a mixture of acetic acid, acetate ester and acetate salt, e.g., in the presence of a catalyst and under a high pressure of hydrogen (e.g., 25 or 50 bar to 700 bar) to produce ethanol.

Figure 7A:
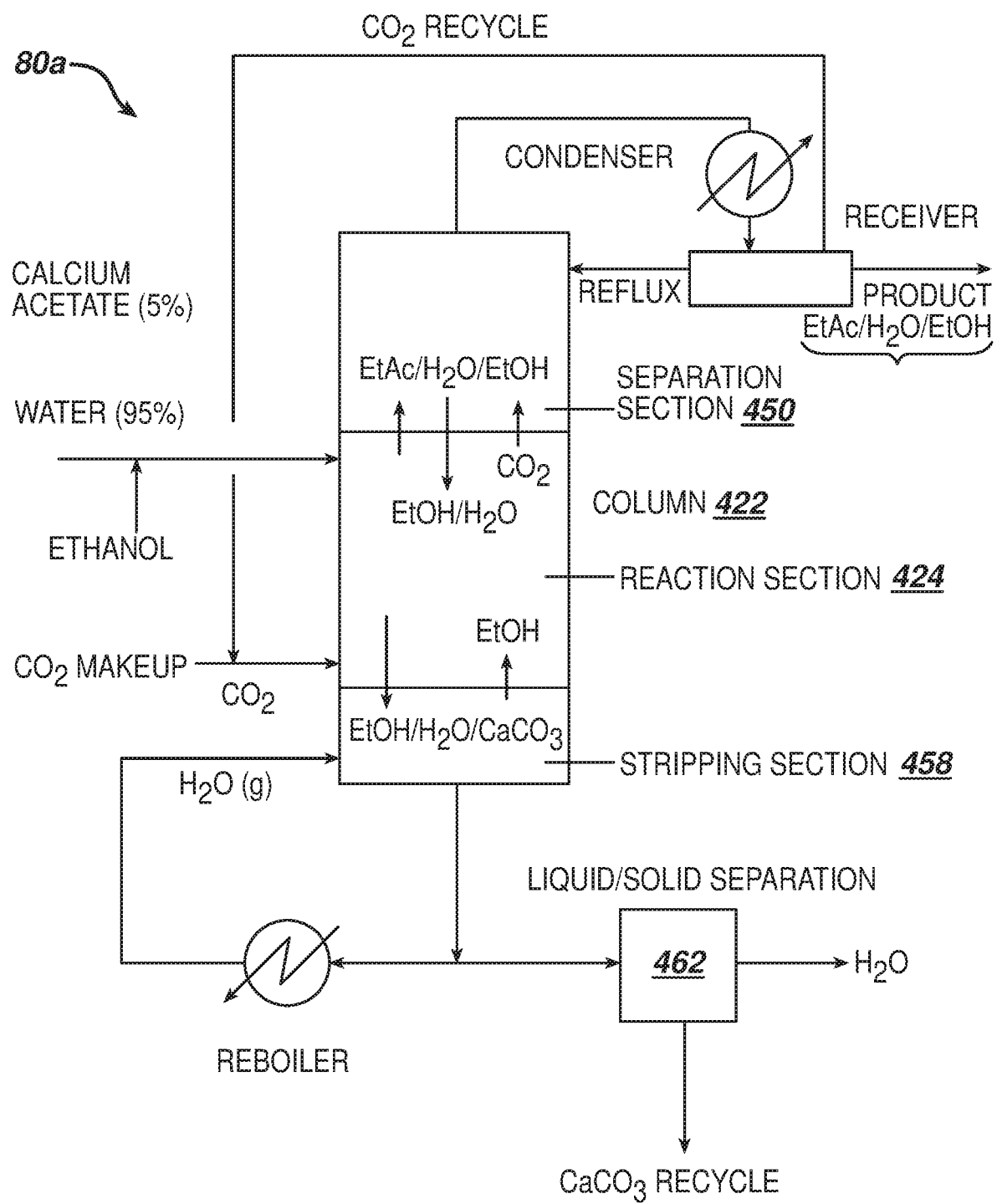
FIG. 7A is a schematic diagram illustrating conversion of calcium acetate and ethanol to ethyl acetate.

In some instances, acetate salts are selectively produced, which can be converted to esters (e.g., ethyl esters) using a reactive distillation process 80a that is shown in FIG. 7A.

In the reaction section 424, a dilute (5%) solution of calcium acetate in water is mixed with ethanol and fed to the column 422 at the top of the reaction section. Carbon dioxide is fed to the column 422 at the bottom of the reaction section 424. The simultaneous reaction of carbon dioxide with calcium acetate and ethanol takes place in the reaction zone 424 in the center section of the column 422 with the formation of calcium carbonate and ethyl acetate (EtAc).

The most volatile component in the reaction mixture is the ethyl acetate/water/ethanol azeotrope. The azeotrope composition is 82.6% ethyl acetate, 9% water and 8.4% ethanol and has a normal boiling point of 70.2° C. The azeotrope is removed from the reaction mixture by vaporization along with some EtOH and water. The bottom product from the reaction zone is a water and ethanol solution containing the suspended calcium carbonate, which flows to the stripping section.

In the upper separation section 450, the azeotrope is separated from the ethanol and water also vaporized from the reaction mixture. The ethanol/water mixture is recycled to the reaction zone 424 and the overhead product is the azeotrope. The carbon dixoxide is separated from the overhead condensate and recycled to the column with makeup carbon dioxide. The azeotrope can be broken by the addition of water, which causes a phase separation, with the water and ethanol rich phase being returned to the appropriate point in the reactive distillation column.

Since excess ethanol is used to favor the forward esterification reaction in the reaction section, the stripping section 458 returns the excess ethanol to the reaction zone. In the stripping section 458, the ethanol is removed from the calcium carbonate-containing water stream, which is discharged from the column 422 and separated by a liquid/solid separation 462, such as centrifugation or filtration.

The net effect of the reactive distillation process is to recover the acetic acid from the dilute salt solution, thereby producing a relatively concentrated product stream at the top and without vaporizing the water that forms the bulk of the stream. The integration of the three sections reduces the overall energy requirements and the simultaneous removal of the product ester shifts the esterification equilibrium, which gives a higher conversion in a shorter time.

Figure 8:
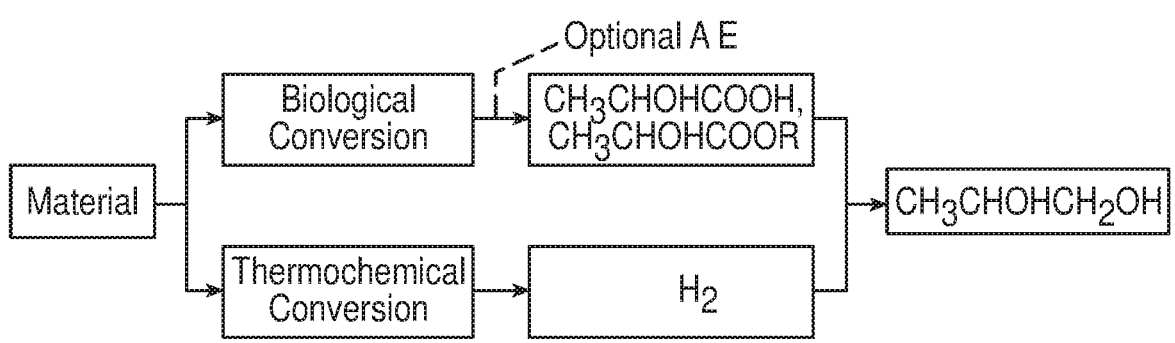
FIG. 8 is a schematic diagram illustrating production of propylene glycol.

Referring now to FIG. 8, one method of producing propylene glycol (propane-1,2-diol) from a material that includes carbon-containing compounds, such as a lignocellulosic material treated with accelerated electrons in which less than about 75% by weight of the carbon-containing compounds are in the form of carbohydrates, includes biologically converting (without or without enzymatic assistance) a portion of the material into lactic acid, a lactate ester, a lactate salt, or mixtures thereof (shown as simply $CH_3CH(OH)COOH$ and $CH_3CH(OH)COOR$ in the figure) and converting another portion of the material using a thermochemical process (e.g., gasification) to produce a syngas (shown in the figure as $H_2$). The syngas is then reacted with the lactic acid, a lactate ester, a lactate salt, or mixtures thereof, e.g., in the presence of a catalyst and under a high pressure of hydrogen (e.g., 25 or 50 bar to 700 bar) to produce propylene glycol.

Utilizing processes analogous to those discussed herein, carbon-containing materials can be utilized to produce n-propanol, e.g., from a mixture that includes propionic acid, a propionate ester, a propionate salt, acetic acid, an acetate ester, an acetate salt or a mixture thereof.

Utilizing processes analogous to those discussed herein, carbon-containing materials can be utilized to produce butanol and ethanol, e.g., from a mixture that includes butyric acid, a butyrate ester, a butyrate salt, acetic acid, an acetate ester, an acetate salt or a mixture of butyric acid, butyrate ester, butyrate salt, acetic acid, acetate ester and acetate salt.

Utilizing processes analogous to those discussed herein, carbon-containing materials can be utilized to produce 1,4-butanediol, e.g., from a mixture that includes succinic acid, a succinate ester, a succinate salt, or a mixture of succinic acid, succinate ester and succinate salt.

Utilizing processes analogous to those discussed herein, carbon-containing materials can be utilized to produce 1,3-propanediol, e.g., from a mixture that includes 3-hydroxypropionic acid, 3-hydroxypropionate ester, 3-hydroxypropionate salt, or a mixture of 3-hydroxypropionic acid, 3-hydroxypropionate ester and 3-hydroxypropionate salt.

Other Embodiments

A number of embodiments have been described. Nevertheless, it will be understood that various modifications may be made without departing from the spirit and scope of the disclosure.

For example, while syngas and syngas components can be produced on-site from a carbon-containing material feedstock, the syngas or any component thereof can also be purchased, e.g., from an oil refinery.

While it is possible to perform all the processes described herein all at one physical location, in some embodiments, the processes are completed at multiple sites. For example, the ester mixtures can be transported to a high-pressure hydrocracker at another physical location.

While the techniques presented herein work with carbon-containing biomass materials, they also work with any of the other carbon-containing materials described herein, such as coal, sugar and starch. For example, coal or starch can be irradiated and then converted into organic acids, salts or acids and/or esters of organic acids.

Any carbon dioxide generated and/or lignin liberated in any process described herein can be captured. Any captured carbon dioxide can be sequestered, e.g., by injecting the captured carbon dioxide into a geological formation, such as an unmineable coal seam or a deep saline aquifer capable of maintaining the carbon dioxide, e.g., for a period of time greater than 100 years, e.g., greater than 250 years, 500 years, 1,000 years or greater than 10,000 years. For example, any carbon dioxide produced in any process described herein can be sequestered, e.g., by fixing carbon dioxide utilizing any microorganism described herein. For example, the microorganism can include algae and the carbon dioxide can be sequestered in the form of a carbohydrate and/or lipid. If desired, e.g., to produce a bio-diesel, the lipid can be converted into an ester, e.g., a methyl, ethyl, n-propyl, isopropyl or butyl ester. Any ester can be converted to alcohol, e.g., by hydrogenating, as described herein.

Figure 9:
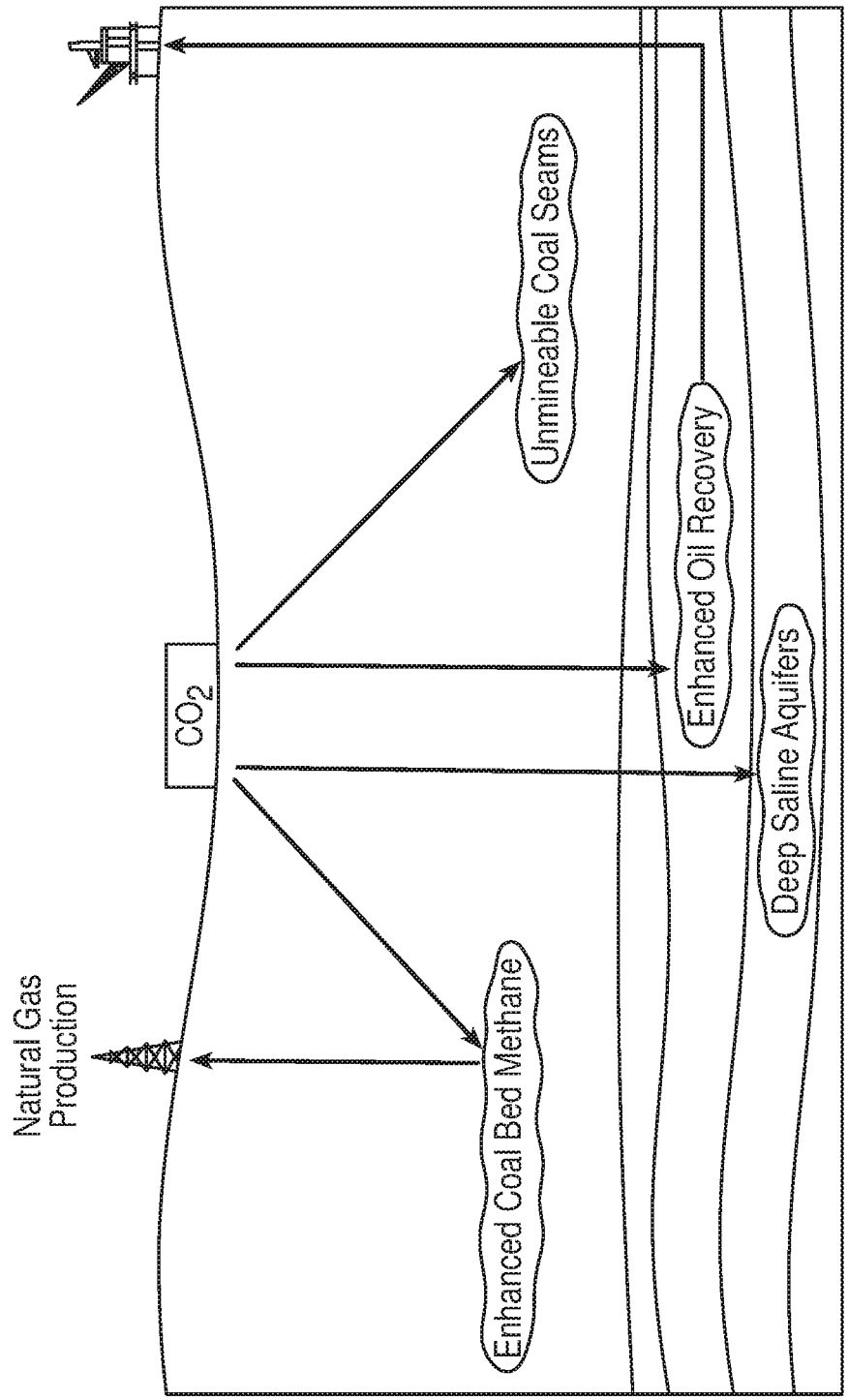
FIG. 9 is a schematic drawing illustrating carbon capture in various geological formations.

Referring now to FIG. 9, carbon dioxide emissions can be stored in various geological formations. For example, the carbon dioxide can be stored in a deep saline aquifer or in an unmineable coal seam. The carbon dioxide can also be used to expel from the earth hard to get at natural gas or oil.

Carbon dioxide can also be captured and used in the food and beverage industry. For example, the carbon dioxide can be converted into dry ice, or it can be utilized in carbonated beverages.

Figure 10:
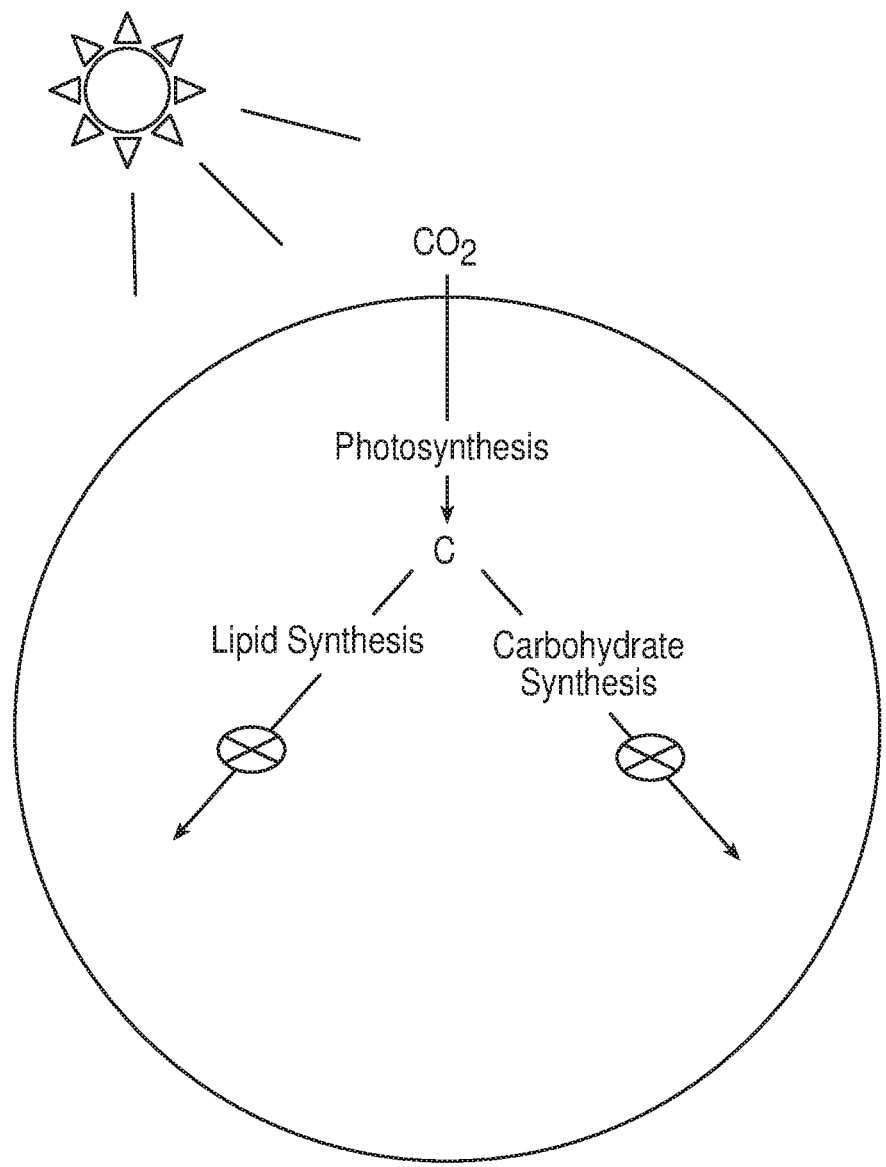
FIG. 10 is a schematic drawing illustrating photosynthesis of carbohydrates and lipids.
Figure 10:
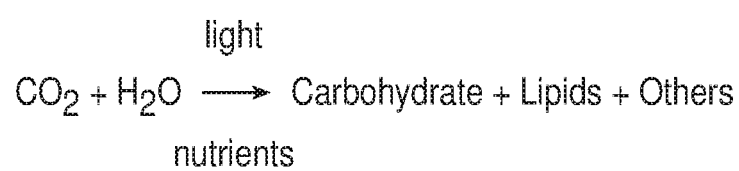

Referring to FIG. 10, any microorganism described herein that is capable of fixing carbon dioxide can be utilized in sequestering carbon dioxide. In particular, FIG. 10 illustrates a photosynthetic pathway in which carbon dioxide in the presence of light, water, nutrients and a microorganism capable of fixing carbon dioxide is converted into various products, including carbohydrates and lipids. The carbohydrates generated can be utilized in any process described herein, such as for the making ethanol, and the lipids can be, e.g., converted into bio-diesel, used in food or as dietary supplements.

Suitable algae include microalgae, such as diatoms and cyanobacteria, and macroalgae, e.g., seaweed. Specific examples include *Botryococcus braunii*, *Chlorella*, *Dunaliella tertiolecta*, *Gracilaria*, *Pleurochrysis carterae* (also called CCMP647), and *Sargassum*.

Figure 11:
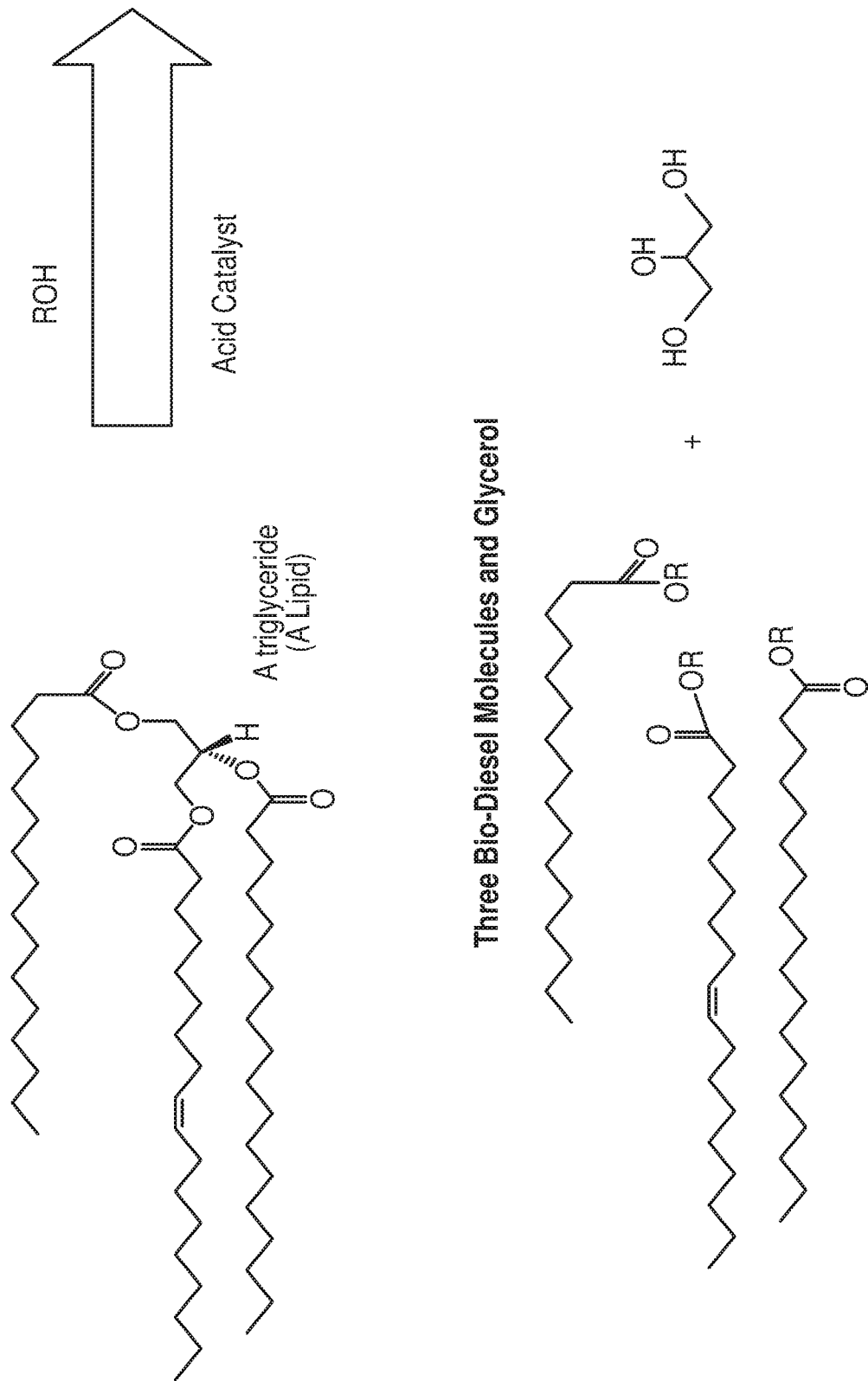
FIG. 11 is a schematic drawing illustrating production of bio-diesel.

Referring now to FIG. 11, a lipid, such as a triglyceride (fat), can be converted to bio-diesel by esterification using an alcohol (ROH) and a catalyst, such as an acid, such as a mineral acid (e.g., sulfuric acid). As shown, for each molecule of triglyceride, three molecules of bio-diesel are formed, along with one molecule of glycerol.

Figure 12A:
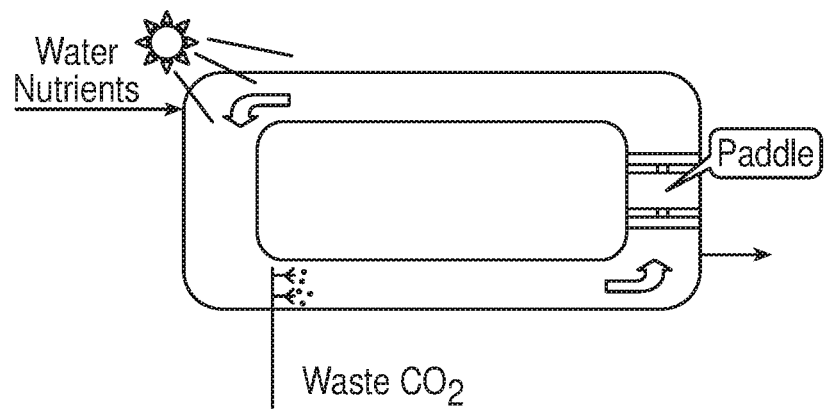
FIG. 12A is an enlarged view of region 12.
Figure 12:
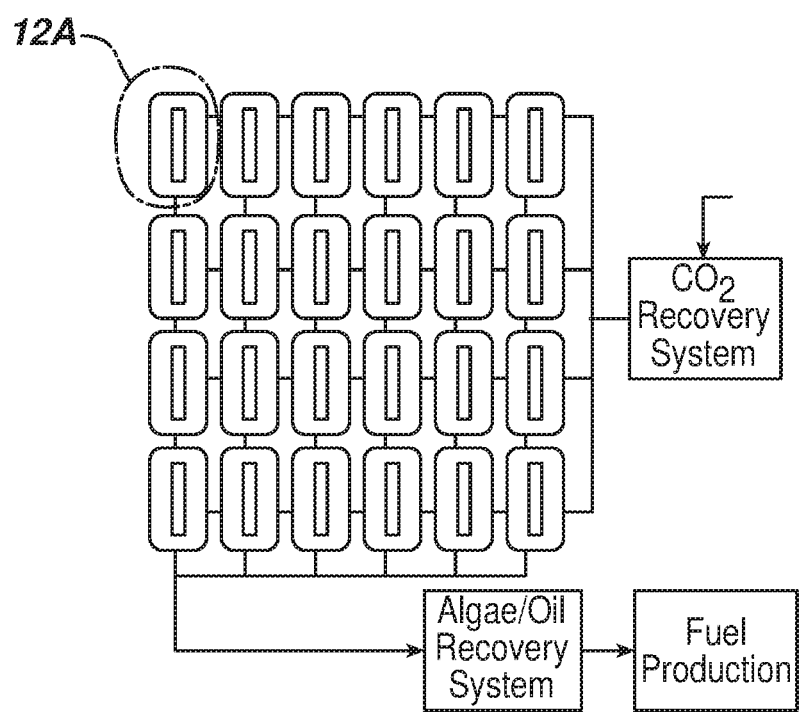

Referring now to FIGS. 12 and 12 A, waste carbon dioxide and nutrients can be fed to a circulating reaction vessel that contains algae suspended in a solvent, such as water. A light source, such as the sun or an artificial light source shines on the materials in the reaction vessel as the paddle wheel continuously circulates the materials. After a desired amount of product, such as one or more carbohydrates and/or one or more lipids is produced, the contents of the reactor are emptied and the oil is recovered and converted into a desired fuel, such as a diesel.

Lignin liberated in any process described herein can be captured and utilized. For example, the lignin can be used as captured as a plastic, or it can be synthetically upgraded to other plastics. In some instances, it can be utilized as an energy source, e.g., burned to provide heat. In some instances, it can also be converted to lignosulfonates, which can be utilized as binders, dispersants, emulsifiers or as sequestrants.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer.

As a dispersant, the lignin or lignosulfonates can be used, e.g., concrete mixes, clay and ceramics, dyes and pigments, leather tanning and in gypsum board.

As an emulsifier, the lignin or lignosulfonates can be used, e.g., in asphalt, pigments and dyes, pesticides and wax emulsions.

As a sequestrant, the lignin or lignosulfonates can be used, e.g., in mico-nutrient systems, cleaning compounds, and water treatment systems, e.g., for boiler and cooling systems.

As a heating source, lignin generally has a higher energy content than holocellulose (cellulose and hemicellulose) since it contains more carbon than holocellulose. For example, dry lignin can have an energy content of between about 11,000 and 12,500 BTU per pound, compared to 7,000 an 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, such as applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Accordingly, other embodiments are within the scope of the following claims.

What is claimed is:

1. A method of processing biomass, the method comprising: treating biomass with radiation, thereby producing treated biomass; and converting a first portion of the treated biomass utilizing bacteria capable of metabolizing both sugar and syngas feedstocks, to produce the carboxylic acid ester, wherein during converting, syngas is delivered to the bacteria, wherein the syngas is produced by gasification of a second portion of the treated biomass.

2. The method of claim 1 wherein the radiation comprises gamma radiation, microwave radiation, infrared radiation, electron beam radiation, X-rays, ultraviolet radiation, ion particle beam radiation, or a combination of any of the forgoing.

3. The method of claim 2 wherein the radiation comprises electron beam radiation.

4. The method of claim 3 wherein the electron beam radiation is delivered at a dose of at least 10 Mrad.

5. The method of claim 1, further comprising treating the biomass with shearing, cutting, grinding, pulverizing, chopping, shredding, sonication, pyrolysis, oxidation, steam explosion, ozone, Fenton's solution, or a combination of any of the foregoing.

6. The method of claim 1 wherein the treated biomass is densified prior to converting.

7. The method of claim 1 wherein the biomass comprises material selected from the group consisting of: paper, paper products, wood, wood-related materials, particle board, grass, rice hulls, bagasse, cotton, jute, hemp, flax, bamboo, sisal, abaca, straw, corn cobs, rice hulls, coconut hair, cotton, algae, seaweed and mixtures of any of these.

8. The method of claim 1, further comprising capturing any lignin liberated.

9. The method of claim 1 wherein the bacteria are anaerobic.

10. The method of claim 1 wherein the carboxylic acid ester is ethyl acetate.

11. The method of claim 1 wherein the carboxylic acid ester is a methyl ester.

12. The method of claim 1 wherein the carboxylic acid ester is an n-propyl ester.

13. The method of claim 1, further comprising hydrogenating the carboxylic acid ester or exposing the carboxylic acid ester to a reducing agent.

* * * * *